(12) United States Patent
Stahmann et al.

(10) Patent No.: US 9,108,062 B2
(45) Date of Patent: Aug. 18, 2015

(54) VENTRICULAR PACING TO AUGMENT ATRIAL NATRIURETIC HORMONE PRODUCTION

(71) Applicant: Cardiac Pacemakers, Inc., St. Paul, MN (US)

(72) Inventors: Jeffrey E. Stahmann, Ramsey, MN (US); Ramesh Wariar, Blaine, MN (US); Stephen B. Ruble, Lino Lakes, MN (US)

(73) Assignee: Cardiac Pacemakers,Inc., St. Paul, MN (US)

( * ) Notice: Subject to any disclaimer, the term of this patent is extended or adjusted under 35 U.S.C. 154(b) by 133 days.

(21) Appl. No.: 14/045,572

(22) Filed: Oct. 3, 2013

(65) Prior Publication Data

US 2014/0031886 A1 Jan. 30, 2014

Related U.S. Application Data

(63) Continuation of application No. 12/966,249, filed on Dec. 13, 2010, now Pat. No. 8,571,656.

(60) Provisional application No. 61/286,532, filed on Dec. 15, 2009.

(51) Int. Cl.
*A61N 1/365* (2006.01)
*A61N 1/362* (2006.01)
*A61N 1/36* (2006.01)

(52) U.S. Cl.
CPC .............. *A61N 1/365* (2013.01); *A61N 1/3627* (2013.01); *A61N 1/36585* (2013.01); *A61N 1/36* (2013.01)

(58) Field of Classification Search
CPC . A61N 1/3627; A61N 1/36585; A61N 1/365; A61N 1/36
See application file for complete search history.

(56) References Cited

U.S. PATENT DOCUMENTS

| 5,137,019 | A | 8/1992 | Pederson et al. |
|---|---|---|---|
| 6,678,547 | B2 | 1/2004 | Carlson et al. |
| 7,189,204 | B2 | 3/2007 | Ni et al. |
| 7,295,874 | B2 | 11/2007 | Prinzen et al. |
| 7,366,568 | B2 | 4/2008 | Pastore et al. |
| 7,437,191 | B2 | 10/2008 | Pastore et al. |
| 7,481,759 | B2 | 1/2009 | Whitehurst et al. |
| 7,499,748 | B2 | 3/2009 | Moffitt et al. |
| 7,566,308 | B2 | 7/2009 | Stahmann |
| 7,572,225 | B2 | 8/2009 | Stahmann et al. |
| 7,574,259 | B1 | 8/2009 | Pei et al. |
| 8,229,557 | B2 | 7/2012 | Patangay et al. |
| 2002/0045810 | A1 | 4/2002 | Ben-Haim |
| 2004/0073128 | A1 | 4/2004 | Hatlestad et al. |
| 2004/0186523 | A1 | 9/2004 | Florio |
| 2005/0288721 | A1 | 12/2005 | Girouard et al. |
| 2007/0055317 | A1 | 3/2007 | Stahmann et al. |

(Continued)

OTHER PUBLICATIONS

"U.S. Appl. No. 12/966,249, Non Final Office Action mailed Jan. 24, 2013", 16 pgs.

(Continued)

*Primary Examiner* — Catherine Voorhees
(74) *Attorney, Agent, or Firm* — Schwegman Lundberg & Woessner, P.A.

(57) ABSTRACT

Intermittent delivery of ventricular pacing pulses synchronized to occur during an atrial diastole time period can be used to provide atrial stretch therapy and augment the production and release of atrial natriuretic hormone.

20 Claims, 6 Drawing Sheets

(56) References Cited

U.S. PATENT DOCUMENTS

| | | |
|---|---|---|
| 2007/0118056 A1 | 5/2007 | Wang et al. |
| 2007/0260285 A1 | 11/2007 | Libbus et al. |
| 2007/0299475 A1 | 12/2007 | Levin et al. |
| 2008/0027495 A1 | 1/2008 | Prinzen et al. |
| 2008/0077187 A1 | 3/2008 | Levin et al. |
| 2008/0081354 A1 | 4/2008 | Qu et al. |
| 2008/0215105 A1 | 9/2008 | Pastore et al. |
| 2008/0221636 A1 | 9/2008 | Pastore et al. |
| 2008/0234774 A1 | 9/2008 | Baynham et al. |
| 2009/0043348 A1 | 2/2009 | Pastore et al. |
| 2009/0192560 A1 | 7/2009 | Arcot-Krishnamurthy et al. |
| 2009/0234401 A1 | 9/2009 | Zielinski et al. |
| 2009/0234416 A1 | 9/2009 | Zielinski et al. |
| 2009/0281591 A1 | 11/2009 | Shuros et al. |
| 2010/0010551 A1 | 1/2010 | Shuros et al. |
| 2010/0016913 A1 | 1/2010 | Arcot-Krishnamurthy et al. |
| 2010/0016916 A1 | 1/2010 | Arcot-Krishnamurthy et al. |
| 2010/0069980 A1 | 3/2010 | Stahmann |
| 2010/0069989 A1 | 3/2010 | Shipley et al. |
| 2010/0087887 A1 | 4/2010 | Dong et al. |
| 2010/0121402 A1 | 5/2010 | Arcot-Krishnamurthy et al. |
| 2010/0305648 A1 | 12/2010 | Arcot-Krishnamurthy et al. |
| 2011/0022127 A1 | 1/2011 | Averina et al. |
| 2011/0144712 A1 | 6/2011 | Stahmann et al. |

OTHER PUBLICATIONS

"U.S. Appl. No. 12/966,249, Notice of Allowance mailed Jun. 25, 2013", 6 pgs.

"U.S. Appl. No. 12/966,249, Response filed Apr. 24, 2013 to Non Final Office Action mailed Jan. 24, 2013", 11 pgs.

Berglund, H., et al., "Haemodynamic and hormonal responses to cardiac pacing in humans: influence of different stimulation sequences and rates.", Clin Sci (Lond), 88(2), (Feb. 1995), 165-72.

Cabello, Juan B, et al., "Acute and chronic changes in atrial natriuretic factor induced by ventricular pacing: a self controlled clinical trial.", Pacing Clin Electrophysiol, 19(5), (May 1996), 815-21.

Clark, B. A., et al., "Effect of atrial natriuretic peptide on potassium-stimulated aldosterone secretion: potential relevance to hypoaldosteronism in man.", J Clin Endocrinol Metab., 75(2), (Aug. 1992), 399-403.

Cody, R. J., et al., "Atrial natriuretic factor in normal subjects and heart failure patients. Plasma levels and renal, hormonal, and hemodynamic responses to peptide infusion.", J Clin Invest., 78(5), (Nov. 1986), 1362-74.

Ellenbogen, K. A, et al., "Atrial natriuretic factor release is enhanced by incremental atrial pacing.", Am Heart J., 116(2 Pt 1). (Aug. 1988), 489-96.

Ganz, M. B, et al., "Atrial natriuretic peptide enhances activity of potassium conductance in adrenal glomerulosa cells.", Am J Physiol., 266(5 Pt 1), (May 1994), C1357-65.

Haufe, M. C, et al., "Acute increase in right atrial pressure by intracardiac stimulation releases atrial natriuretic peptide.", Eur Heart J., 8(3), (Mar. 1987), 277-81.

Horie, Hajime, et al., "Plasma brain natriuretic peptide as a biochemical marker for atrioventricular sequence in patients with pacemakers.", Pacing Clin Electrophysiol., 22(2), (Feb. 1999), 282-90.

Kitakaze, Masafumi, et al., "Human atrial natriuretic peptide and nicorandil as adjuncts to reperfusion treatment for acute myocardial infarction (J-WIND): two randomised trials.", Lancet, 370(9597), (Oct. 27, 2007), 1483-93.

La Villa, Giorgio, et al., "Plasma levels of natriuretic peptides during ventricular pacing in patients with a dual chamber pacemaker.", Pacing Clin Electrophysiol., 17(5 Pt 1), (May 1994), 953-8.

Lee, Candace Y, et al., "Natriuretic peptides and therapeutic applications.", Heart Fail Rev., 12(2), (Jun. 2007), 131-42.

Lo Bianco, T., et al., "[Acute effects of ventricular and bicameral stimulation on plasma levels of natriuretic hormone]", G Ital Cardiol., 27(10), (Oct. 1997), 1019-23.

Malatino, L. S, et al., "Baseline and post-atrial pacing release of atrial natriuretic factor in mitral stenosis.", Am Heart J., 119(1), (Jan. 1990), 97-101.

Melo, Luis Gabriel, et al., "Atrial Natriuretic Peptide: Regulator of Chronic Arterial Blood Pressure.", News Physiol Sci., 15, (Jun. 2000), 143-149.

Noll, B., et al., "Influence of pacing mode and rate on peripheral levels of atrial natriuretic peptide (ANP).", Pacing Clin Electrophysiol., 12(11), (Nov. 1989), 1763-8.

Obata, K., et al., "Increase of human atrial natriuretic polypeptide in response to cardiac pacing.", Am Heart J., 113(3), (Mar. 1987), 845-7.

Obata, K., et al., "Increased secretion of atrial natriuretic polypeptide in response to cardiac pacing.", Jpn Circ J., 53(9), (Sep. 1989), 1055-60.

Papadopoulos, C. L, et al., "ANP concentrations during interchanging DDD-VVI pacing modes in patients with retrograde ventriculoatrial conduction.", Acta Cardiol., 52(1), (1997), 37-47.

Scriven, Terry A., et al., "Effects of synthetic atrial natriuretic peptide on renal function and renin release in acute experimental heart failure.", Circulation, 72(4), (Oct. 1985), 892-7.

Vesely, D. L, et al., "Comparison of vessel dilator and long-acting natriuretic peptide in the treatment of congestive heart failure.", Am Heart J., 138(4 Pt 1), (Oct. 1999), 625-32.

Weil, J., et al., "Plasma atrial natriuretic peptide concentrations during intracardiac pacing", Acta Endocrinol. Suppl. (Copenhagen), 274, (1986), 164-165.

Zullo, Michael A, "Characteristics of the acute rise of atrial natriuretic factor during ventricular pacing.", Chest, 121(6), (Jun. 2002), 1942-6.

VENTRICULAR PACING TO AUGMENT ATRIAL NATRIURETIC HORMONE PRODUCTION

CROSS-REFERENCE TO RELATED APPLICATION

This application is a continuation of U.S. application Ser. No. 12/966,249, filed Dec. 13, 2010, which claims the benefit of U.S. Provisional Application No. 61/286,532, filed on Dec. 15, 2009, under 35 U.S.C. §119(e), which is incorporated herein by reference in its entirety.

BACKGROUND

Atrial natriuretic hormone (ANH)—also referred to as atrial natriuretic peptide (ANP), atrial natriuretic factor (ANF), or atriopeptin—is a polypeptide hormone involved in the homeostatic regulation of body water, sodium, and potassium. ANH is produced, stored, and secreted from atrial myocytes in response to a variety of physiological signals, including atrial stretch, hypervolemia, and stimulation of the sympathetic nervous system, for example. ANH can cause vasodilation and diuresis in response to increased blood pressure and volume. Furthermore, ANH can help inhibit hypertrophy and fibrosis of the myocardium—often referred to as "remodeling"—which can occur during or after an ischemic event, for example. It is also believed that ANH can inhibit the renin-angiotensin-aldosterone system (RAAS), thereby reducing fluid overload and preventing or inhibiting maladaptive cardiac remodeling. Thus, ANH can benefit heart failure patients by reducing the stress of blood volume overload on the heart, as well as inhibiting cardiac remodeling.

OVERVIEW

This document describes, among other things, intermittent delivery of ventricular pacing pulses synchronized to occur during an atrial diastole time period to provide atrial stretch therapy and augment the production and release of atrial natriuretic hormone.

Example 1 can include an apparatus comprising a cardiac rhythm management device comprising: a ventricular pacing circuit, configured to deliver a ventricular pace; and a processor circuit, coupled to the ventricular pacing circuit, the processor configured to comprise a first operating mode, the processor configured to time delivery of the ventricular pace, when in the first operating mode, such that: (1) delivery of the ventricular pace is synchronized to occur during an atrial diastole time period, and (2) delivery of the ventricular pace results in a substantial overlap of ventricular systole and atrial systole.

In Example 2, the subject matter of Example 1 can optionally include the processor being configured to time delivery of the ventricular pace, when in the first operating mode, to cause atrioventricular valve closure during at least one of: early atrial systole or a specified period of time before atrial systole.

In Example 3, the subject matter of any one of Examples 1-2 can optionally include an atrial pacing circuit configured to deliver an atrial pace, and wherein the atrial pacing circuit is coupled to the processor; and wherein the processor is configured to time delivery of the ventricular pace, when in the first operating mode, such that a paced ventricular contraction occurs before a paced atrial contraction during the same cardiac cycle.

In Example 4, the subject matter of any one of Examples 1-3 can optionally include an atrial sensing circuit, coupled to the processor, and configured to sense an atrial heart signal, and wherein the atrial sensing circuit is coupled to the processor; and wherein the processor is configured to time delivery of the ventricular pace, when in the first mode of operation, such that a paced ventricular contraction occurs before a sensed atrial contraction during the same cardiac cycle.

In Example 5, the subject matter of any one of Examples 1-3 can optionally include the processor being configured to time delivery of the ventricular pace, when in the first mode of operation, such that a paced ventricular contraction is substantially concurrent with a paced or sensed atrial contraction during the same cardiac cycle.

In Example 6, the subject matter of any one of Examples 1-5 can optionally include: a physiologic sensor, coupled to the processor, the physiologic sensor configured to measure a physiologic parameter of a subject; wherein the processor is configured to adjust use of the first operating mode using information about the measure of the physiologic parameter.

In Example 7, the subject matter of any one of Examples 1-6 can optionally include: a physical activity sensor, coupled to the processor, the physical activity sensor configured to detect physical activity of a subject; wherein the processor is configured to limit use of the first mode of operation to when the physical activity is above a specified threshold value.

In Example 8, the subject matter of any one of Examples 1-7 can optionally include a cardiac output monitor circuit, coupled to the processor, the cardiac output monitor circuit configured to provide an indication of a cardiac output of the subject; and wherein the processor is configured to limit use of the first mode of operation to when the indication of the cardiac output is below a specified threshold value.

In Example 9, the subject matter of any one of Examples 1-8 can optionally include: a fluid status monitor circuit, coupled to the processor, the fluid status monitor circuit configured to monitor a fluid status providing an indication of a fluid status of the subject; and wherein the processor is configured to use information about the fluid status of the subject to trigger use of the first operating mode.

In Example 10, the subject matter of any one of Examples 1-9 can optionally include the processor being configured to adjust use of the first operating mode when the fluid status indicates at least one of: (1) a fluid overload condition, or (2) a fluid underload condition.

In Example 11, the subject matter of any one of Examples 1-10 can optionally include a fluid status monitor circuit that is configured to monitor the fluid status using a pulmonary artery pressure (PAP) signal received from a PAP sensor.

In Example 12, the subject matter of any one of Examples 1-11 can optionally include the processor circuit being configured to alter a delivery time of the ventricular pace, when in the first operating mode, to provide variability, with respect to an atrial contraction time, over a plurality of the ventricular paces.

In Example 13, the subject matter of any one of Examples 1-12 can optionally include the processor being configured to alter a ventricular pacing site, such as to inhibit or prevent accommodation of the subject to the first operating mode.

In Example 14, the subject matter of any one of Examples 1-13 can optionally include the processor being configured to adjust delivery of a therapy to offset a decrease in cardiac output otherwise associated with the first operating mode.

In Example 15, the subject matter of any one of Examples 1-14 can optionally include the processor being configured to at least one of trigger or inhibit the first operating mode at least in part using information about a detected physiological condition.

In Example 16, the subject matter of any one of Examples 1-15 can optionally include the processor being configured to at least one of trigger or inhibit the first operating mode at least in part using information about a time of day.

In Example 17, the subject matter of any one of Examples 1-16 can optionally include the processor being configured to at least one of trigger or inhibit the first operating mode at least in part using information about a posture.

In Example 18, the subject matter of any one of Examples 1-17 can optionally include the processor being configured to at least one of trigger or inhibit the first operating mode at least in part using information about a sleep state.

Example 19 can include, or can optionally be combined with the subject matter of any one of Examples 1-18 to include an apparatus comprising a cardiac rhythm management device comprising: a ventricular pacing circuit, configured to deliver a ventricular pace; a processor circuit, coupled to the ventricular pacing circuit, the processor configured to comprise a first operating mode, the processor configured to time delivery of the ventricular pace, when in the first operating mode, such that: (1) delivery of the ventricular pace is synchronized to occur during an atrial diastole time period, (2) delivery of the ventricular pace results in a substantial overlap of ventricular systole and atrial systole, and (3) atrioventricular valve closure is caused during at least one of: early atrial systole or a specified period of time before atrial systole; a physiologic sensor, coupled to the processor, the physiologic sensor configured to measure a physiologic parameter of a subject including a physical activity, a cardiac output, and a fluid status; wherein the processor is configured to adjust use of the first operating mode using information about the measure of the physiologic parameter, including using information about the fluid status and including limiting use of the first mode of operation to when the physical activity is above a specified threshold value and to when cardiac output is below a specified threshold value; and wherein the processor is configured to provide variability in the first operating mode to inhibit or prevent accommodation of the subject to the first operating mode.

In Example 20, the subject matter of any one of Examples 1-19 can optionally include the processor being configured to adjust delivery of a therapy to offset a decrease in cardiac output otherwise associated with the first operating mode.

In Example 21, the subject matter of any one of Examples 1-20 can optionally include the processor is configured to at least one of trigger or inhibit the first operating mode at least in part using time of day, posture, or sleep status information.

Example 22 can include, or can optionally be combined with the subject matter of any one of Examples 1-21 to include an apparatus comprising a cardiac rhythm management device comprising: a ventricular pacing circuit, configured to deliver a ventricular pace; a processor circuit, coupled to the ventricular pacing circuit, the processor configured to comprise a first operating mode, the processor configured to time delivery of the ventricular pace, when in the first operating mode, such that: (1) delivery of the ventricular pace is synchronized to occur during an atrial diastole time period, and (2) delivery of the ventricular pace results in a substantial overlap of ventricular systole and atrial systole; an atrial pacing circuit configured to deliver an atrial pace, and wherein the atrial pacing circuit is coupled to the processor; and wherein the processor is configured to time delivery of the ventricular pace, when in the first operating mode, such that a paced ventricular contraction occurs before or substantially concurrent with a paced atrial contraction during the same cardiac cycle.

Example 23 can include, or can optionally be combined with the subject matter of one of Examples 1-22 to include a method comprising: using a cardiac rhythm management device, delivering a ventricular pace to a ventricle of a subject when in a first operating mode; and timing delivery of the ventricular pace, when in the first operating mode, such that: (1) delivery of the ventricular pace is synchronized to occur during an atrial diastole time period, and (2) delivery of the ventricular pace results in a substantial overlap of ventricular systole and atrial systole.

In Example 24, the subject matter of any one of Examples 1-23 can optionally include timing delivery of the ventricular pace, when in the first operating mode, includes timing delivery of the ventricular pace to cause atrioventricular valve closure during at least one of: early atrial systole or a specified period of time before atrial systole.

In Example 25, the subject matter of any one of Examples 1-24 can optionally include timing delivery of the ventricular pace, when in the first operating mode, comprises delivering the ventricular pace such that a paced ventricular contraction occurs before a paced atrial contraction during the same cardiac cycle.

In Example 26, the subject matter of any one of Examples 1-25 can optionally include timing delivery of the ventricular pace, when in the first operating mode, comprises delivering the ventricular pace such that a paced ventricular contraction occurs before a sensed atrial contraction during the same cardiac cycle.

In Example 27, the subject matter of any one of Examples 1-25 can optionally include timing delivery of the ventricular pace, when in the first operating mode, comprising delivering the ventricular pace such that a paced ventricular contraction is substantially concurrent with a paced or sensed atrial contraction during the same cardiac cycle.

In Example 28, the subject matter of any one of Examples 1-27 can optionally include: detecting a measure of a physiological parameter of the subject; and adjusting use of the first operating mode using information about the measure of the physiological parameter.

In Example 29, the subject matter of any one of Examples 1-28 can optionally include detecting a physical activity of the subject; and limiting use of the first mode of operation to when the physical activity is above a specified threshold value.

In Example 30, the subject matter of any one of Examples 1-29 can optionally include monitoring a fluid status providing an indication of a fluid status of the subject; and using information about the fluid status of the subject to trigger use of the first operating mode.

In Example 31, the subject matter of any one of Examples 1-30 can optionally include adjusting use of the first operating mode when the fluid status indicates at least one of: (1) a fluid overload condition, or (2) a fluid underload condition.

In Example 32, the subject matter of any one of Examples 1-31 can optionally include monitoring the fluid status comprises monitoring information about a pulmonary artery pressure (PAP).

In Example 33, the subject matter of any one of Examples 1-32 can optionally include altering a delivery time of the ventricular pace, when in the first operating mode, to provide variability, with respect to an atrial contraction time, over a plurality of the ventricular paces.

In Example 34, the subject matter of any one of Examples 1-33 can optionally include adjusting delivery of a therapy to offset a decrease in cardiac output otherwise associated with the first operating mode.

In Example 35, the subject matter of any one of Examples 1-34 can optionally include at least one of triggering or inhibiting the first operating mode at least in part using information about a detected physiological condition.

In Example 36, the subject matter of any one of Examples 1-35 can optionally include at least one of triggering or inhibiting the first operating mode at least in part using information about a time of day.

In Example 37, the subject matter of any one of Examples 1-36 can optionally include at least one of triggering or inhibiting the first operating mode at least in part using information about a posture.

In Example 38, the subject matter of any one of Examples 1-37 can optionally include at least one of triggering or inhibiting the first operating mode at least in part using information about a sleep state.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that the timing of ventricular pacing pulse delivery can be adjusted, such as to intermittently stretch the atria, thereby inducing the production and release of ANH. For example, delivery of ventricular pacing pulses that are synchronized to occur during atrial diastole can cause atrial and ventricular systoles to substantially overlap. In other words, such timing of ventricular pacing can result in the in the atria contracting against closed atrioventricular (AV) valves. This can cause an increase in atrial pressure, stretching of the atrial myocardium, and, consequently, augmented production and secretion of ANH.

Such ventricular pacing, synchronized to occur during atrial diastole and intended to augment the release of ANH, can result in at least partial overlap of atrial and ventricular systoles. Although existing devices and algorithms can provide ventricular pacing during atrial diastole, they typically do not cause an overlap of atrial and ventricular systoles. Existing devices, however, could easily be modified, for example, such as by programming the AV delay to be longer than an atrial systole time period, thereby resulting in overlap of atrial and ventricular systoles.

Figure 1:
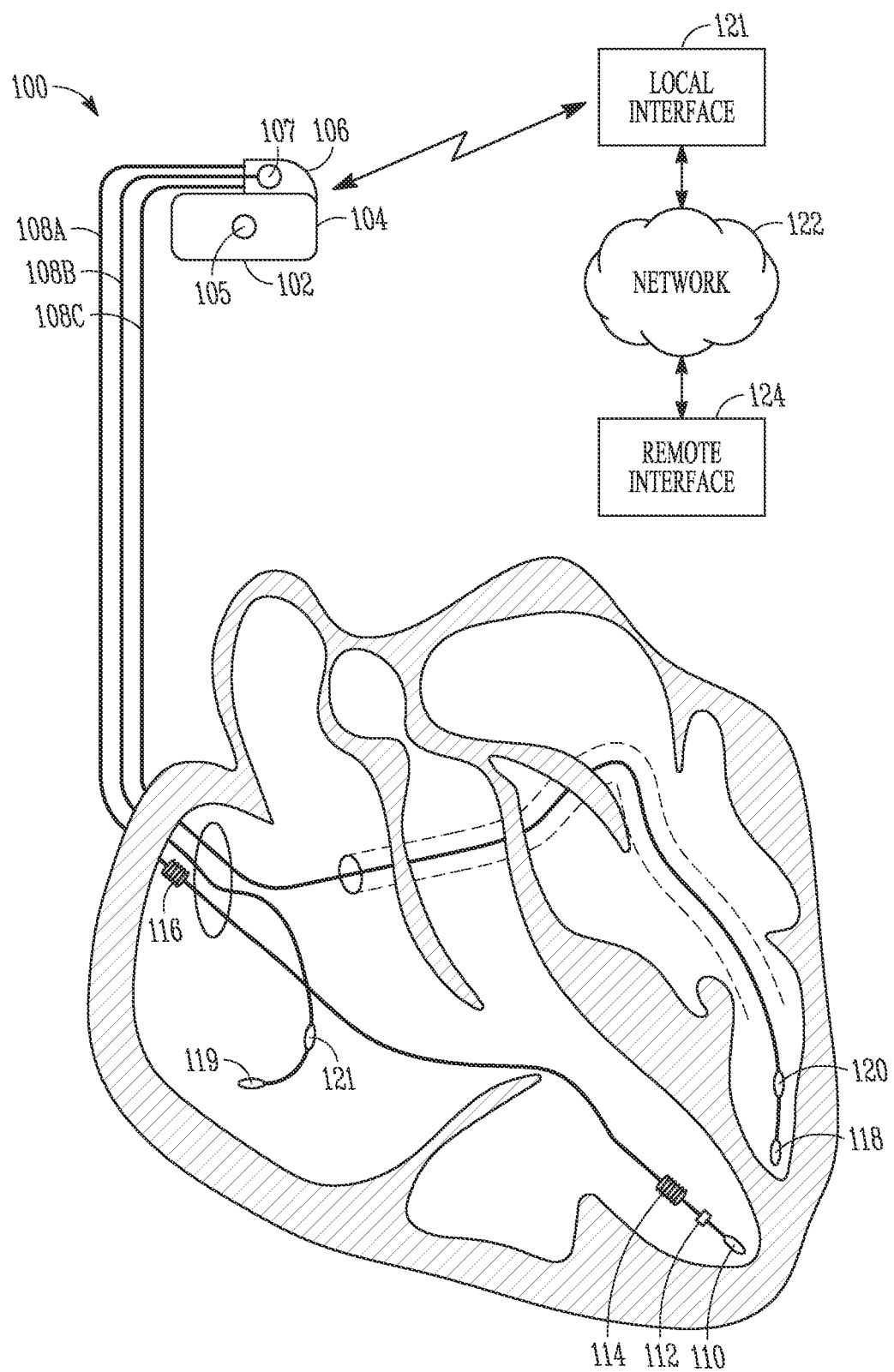
FIG. 1 is a schematic diagram illustrating generally an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular CS/LV lead 108C can extend from the SVC into the RA, through a coronary sinus (CS) into the coronary vasculature, such as near a portion of a left ventricle (LV). In an example, this second CS/LV lead 108C can include at least a distal electrode 118 and a proximal electrode 120, from which electrostimulation energies can be delivered or intrinsic electrical heart signals can be sensed. An intravascular right atrial (RA) lead 1088B can extend from the SVC into the RA, and can include a distal electrode 119 and a proximal electrode 121. Other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

Figure 2:
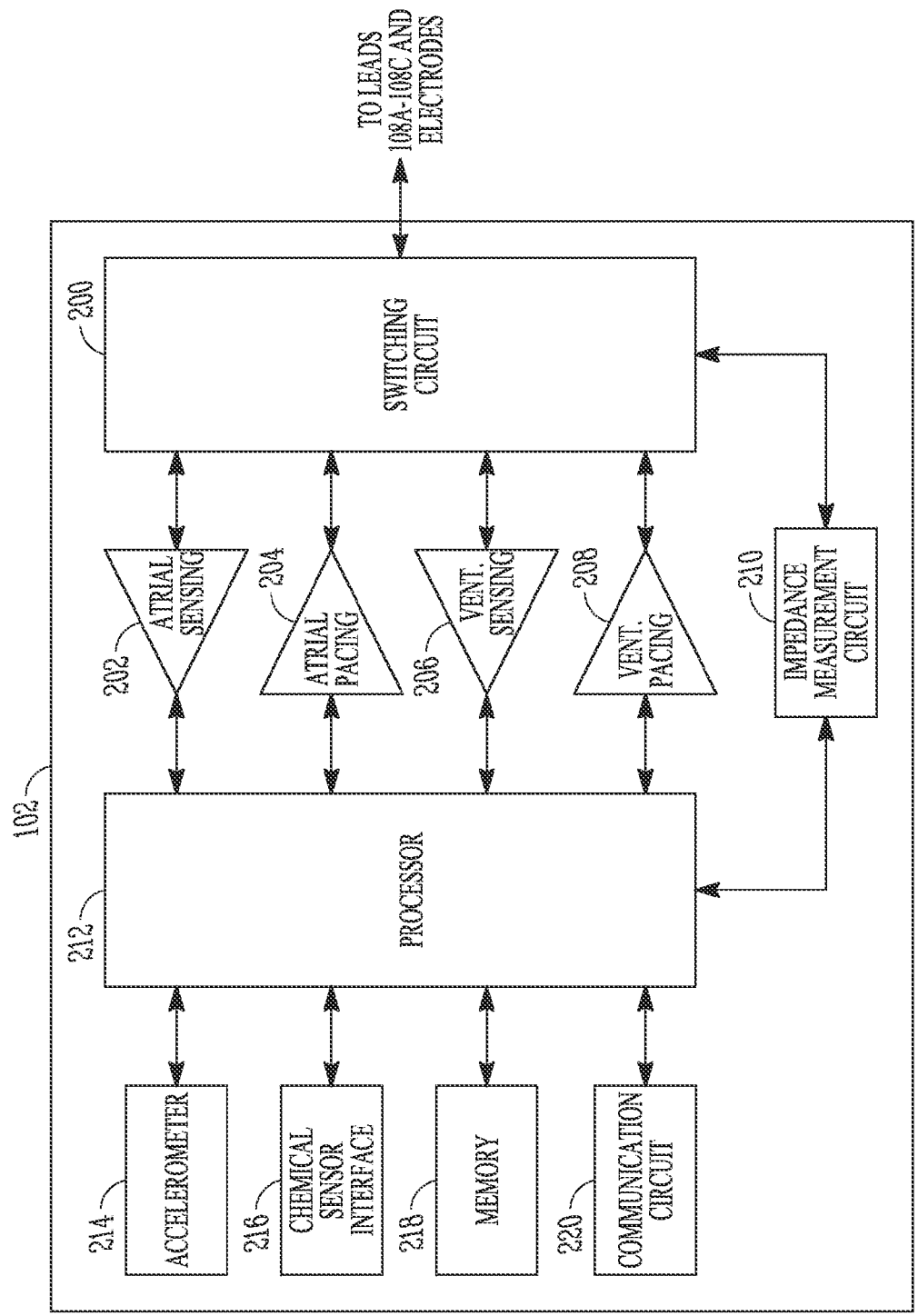
FIG. 2 is a block diagram illustrating generally an example of portions of the CRM device electronics unit.

FIG. 2 shows an example of portions of the CRM device electronics unit 102. In an example, this can include a switching circuit 200, such as for selectively connecting to the various electrodes such as on the leads 108A-C or elsewhere. An atrial sensing circuit 202 and a ventricular sensing circuit 206 can be selectively coupled to various electrodes by the switching circuit 200, and can include sense amplifiers, filter circuits, other circuits such as for sensing intrinsic electrical signals, such as intrinsic heart signals. An atrial pacing circuit 204 and a ventricular pacing circuit 208 can be selectively coupled to various electrodes by the switching circuit 200, and can include pacing energy generation circuitry (e.g., capacitive, inductive, or other) such as for generating, storing, or delivering an electrostimulation or other energy. An impedance measurement circuit 210 can be selectively coupled to various electrodes by the switching circuit 200, such as for measuring a lead impedance, a tissue impedance, a regional or organ impedance, or other impedance. Impedance measurements can be used, for example, to determine a fluid status or a respiration parameter. Another circuit for monitoring one or both of these parameters can additionally or alternatively be included in the CRM device 100. For example, for monitoring fluid status, a pulmonary artery pressure (PAP) sensor interface circuit can be used to receive PAP information from a PAP sensor. Examples of using a PAP sensor are described in Stahmann U.S. patent application Ser. No. 11/249,624, entitled "METHOD AND APPARATUS FOR PULMONARY ARTERY PRESSURE SIGNAL ISOLATION," filed on Oct. 13, 2005, now issued as U.S. Pat. No. 7,566,308, assigned to Cardiac Pacemakers, Inc., which is incorporated herein by reference in its entirety, including its description of obtaining PAP information. In an example, the atrial sensing circuit 202, the atrial pacing circuit 204, the ventricular sensing circuit 206, the ventricular pacing circuit 208, or the impedance circuit 210 can be coupled to a processor circuit 212. In an example, the processor 212 can perform instructions, such as for signal processing of signals derived by the atrial sensing circuit 202, the ventricular sensing circuit 206, or the impedance circuit 210, or for controlling operation of the atrial pacing circuit 204, the ventricular pacing circuit 208, or other operations of the CRM device 100. In an example, the processor 212 can be coupled to or include a physical activity sensor, such as an accelerometer 214, configured to sense a patient's physical activity level. In an example, the accelerometer 214 can further be configured to sense heart sounds or posture. In an example, the processor 212 can be coupled to or include a physiologic sensor interface, such as a chemical sensor interface 216, configured to communicate with a chemical sensor. Examples of chemical sensors that can be used in conjunction with CRM device 100 include sensors configured to measure blood gases, electrolytes, creatinine, blood urea nitrogen, glucose, and natriuretic peptides, among other things. The processor 212 can also be coupled to or include a memory circuit 218, such as for storing or retrieving instructions or data, or a communication circuit 220, such as for communicating with the local interface 121.

CRM device 100 can be configured to operate in a normal operating mode or an ANH-promoting operating mode. In an example, the normal operating mode can be an ongoing normal ventricular pacing mode, such as VVI, VVIR, DDD, DDDR, DDI, DDIR, VDD, VDDR, VOO, or DOO. In another example, the normal operating mode can be an ongoing ventricular sensing mode during which a subject's intrinsic ventricular beats are sensed and no ventricular pacing is provided when an intrinsic ventricular beat is sensed. In an example, the ANH-promoting operating mode can be a special operating mode that can include intermittent delivery of atrial stretch therapy, which can include delivery of ventricular pacing pulses that are synchronized to occur during an atrial diastole time period.

In an example, atrial diastole, which can be thought of as the time period during which the atria are relaxed, can be detected, such as by using an electrogram (EGM) or electrocardiogram (ECG). In an example, an intracardiac EGM can be detected using leads 108A-C and associated electrodes. The P-wave of an EGM or ECG can represent the wave of depolarization that spreads through the atria, causing them to contract. Thus, the P-to-P interval can be used to represent the total time of a single cardiac cycle (e.g., the time from one heart beat to the next). Within the P-to-P interval, a specified time period, such as for example 100 milliseconds, can be designated for atrial systole (e.g., the time period when the atria are contracting). Once a specified time period has been designated for atrial systole, the remainder of the P-to-P interval can be designated as atrial diastole. Thus, the atrial diastole time period can be designated as the P-to-P interval time period minus the atrial systole time period.

In another example, the atrial diastole time period can be estimated as beginning with first heart sound ("S1") and extending for an interval defined by the S1-to-S1 interval minus a specified estimated or measured atrial systolic interval (e.g., 100 ms). S1 is the vibrational sound made by the heart when the AV valves (e.g., mitral and tricuspid valves) close. A second heart sound ("S2") is the vibrational sound made by the heart when the semilunar valves (e.g., aortic and pulmonic valves) close. Although the time period between S1 and S2 can be used as a measure of ventricular systole, it can also be used to estimate the atrial diastole time period.

When CRM device 100 is in the normal operating mode (e.g., under normal conditions), the ventricles can be paced or sensed during atrial systole, such that the ventricles contract at the end of the atrial systole time period, mimicking a normal physiologic cardiac cycle. In an example, a normal cardiac cycle can be defined as the time period between one ventricular contraction and the next ventricular contraction. When CRM device 100 is in the ANH-promoting operating mode, the ventricles can generally be paced or sensed as in the normal operating mode, but, intermittently, ventricular pacing pulses can be delivered during an atrial diastole time period, such that intermittently the ventricles contract at the beginning of atrial systole or before atrial systole. This intermittent, specialized ventricular pacing can be referred to as "ANH pacing" or "ANH pacing cycle(s)."

An example of a method of configuring CRM device 100 to synchronize the timing of the ventricular pace on an atrial sensed or paced event includes utilization of a NASPE/BPEG (North American Society of Pacing and Electrophysiology/British Pacing and Electrophysiology Group) pacing mode. Pacing modes that do not synchronize the timing of the ventricular pace on a sensed or paced atrial event include, for example, VOO, VVI and VVIR. Pacing modes that can synchronize the timing of the ventricular pace on an atrial sensed or paced event include, for example, DDI, VDD, DDD, VDDR, DDDR.

There can be methods other than utilization of a NASPE/BPEG pacing mode by which the ventricular pace can be synchronized to an atrial event. An atrial event can be determined via a measurement other than detection of a p-wave or delivery of an atrial pace. For example, a blood pressure or thoracic impedance measurement can be used to determine an atrial event, such as described in Pederson et al. U.S. Pat. No. 5,137,019 entitled "VARIATION IN CARDIAC CHAMBER VOLUME OR PRESSURE AS A CONTROLLING PARAMETER, assigned to the assignee of the present patent application, the disclosure of which is incorporated herein by reference in its entirety. The timing of the ventricular pace can then be synchronized to the blood pressure or thoracic impedance measurement.

Figure 3A:
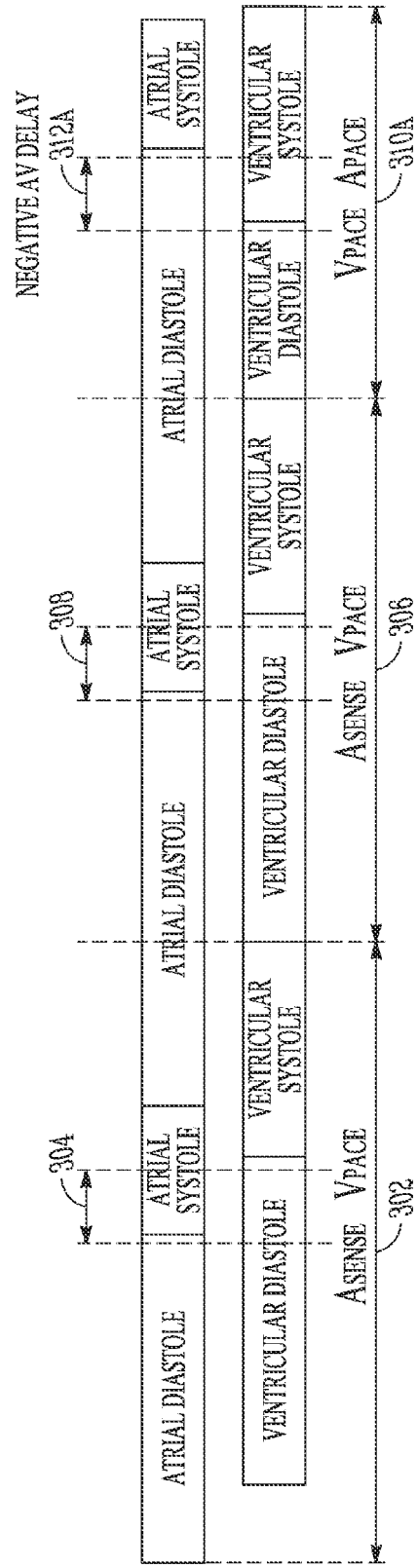
FIGS. 3A-3C are schematic diagrams illustrating generally examples of specialized ventricular pacing used to provide atrial stretch therapy.
Figure 3B:
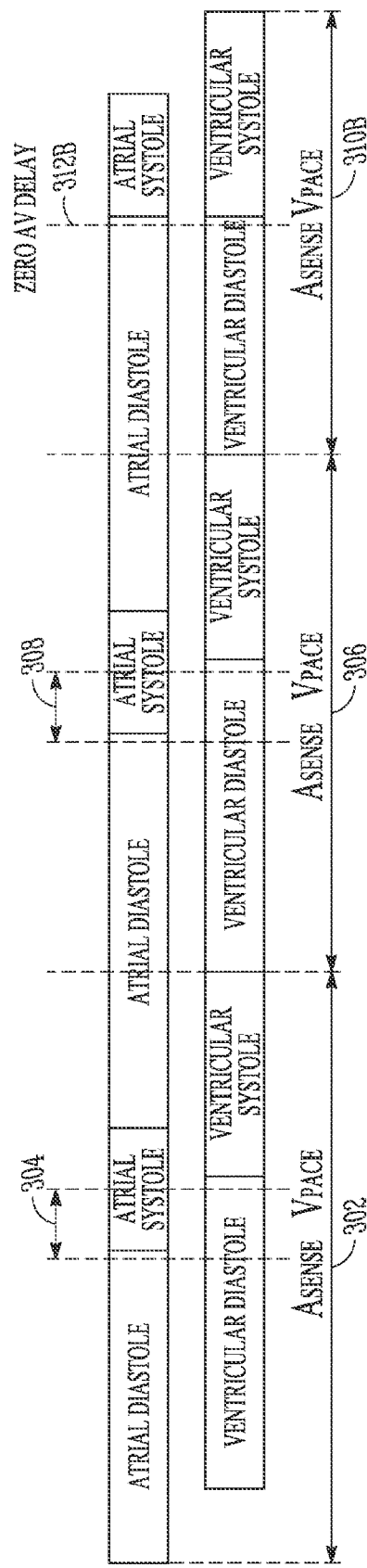
Figure 3C:
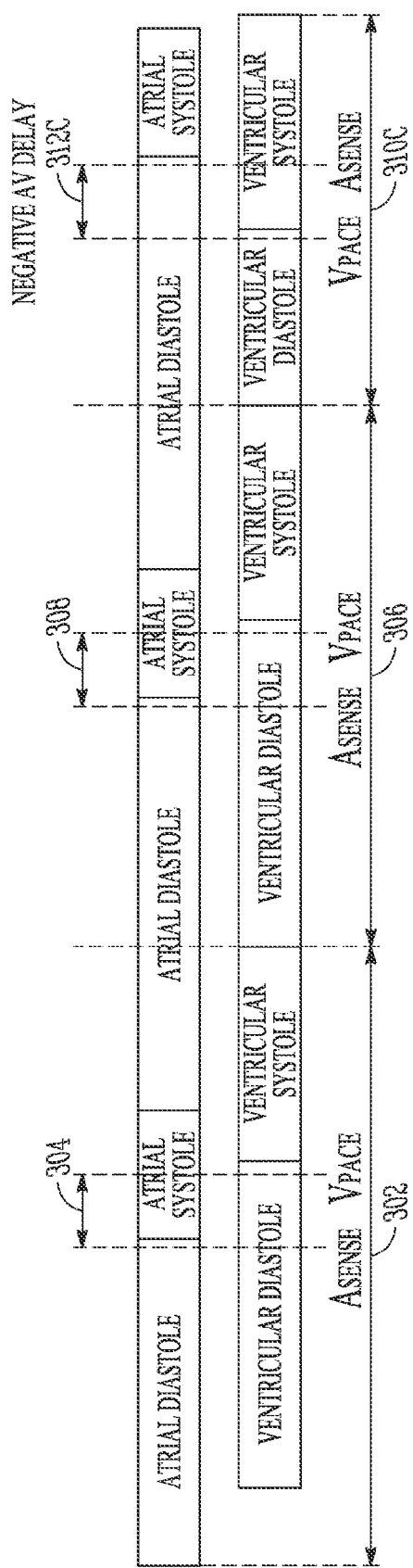

FIGS. 3A-3C are schematic diagrams illustrating generally examples of specialized ventricular pacing that can be used to provide atrial stretch therapy. In the examples shown in FIGS. 3A-C, the CRM device 100 is in the ANH-promoting operating mode. In FIG. 3A, a time period 302 represents a first normal cardiac cycle and a time period 306 represents a second normal cardiac cycle. During time periods 302 and 306, the CRM device 100 can deliver ventricular pacing pulses at the end of atrial systole. In an example, during time periods 302 and 306, the CRM device 100 can sense, rather than pace, ventricular contraction events near the end of atrial systole. Similarly, although the atrial contraction events shown during the time periods 302 and 306 are sensed events, these atrial events can be paced events in some examples. As shown at 304 and 308, respectively, the AV delay in a normal cardiac cycle (e.g., the delay between a sensed atrial event and a paced ventricular event) can be a positive value, such as a value that is between about 10-400 milliseconds, inclusive, for example.

The time period 310A represents an ANH pacing cycle. During the time period 310A, the CRM device 100 can deliver ventricular pacing pulses during atrial diastole. As shown at 310A, during ANH pacing, ventricular systole and atrial systole can substantially overlap. In the example shown at 310A, a ventricular pace is delivered before an atrial pace. As shown at 312A, this creates a negative AV delay. Because a ventricular contraction causes the AV valves to close, ANH pacing can result in the atria contracting against closed AV valves. As blood-filled atria contract against closed AV valves, atrial pressure can increase, causing atrial stretch. Atrial stretch, in turn, can augment the production and release of ANH.

ANH release can be beneficial, and, in an example, ANH pacing can be delivered continuously. However ANH pacing can be less efficient if performed for extended periods of time due to inefficient heart pumping, which can cause a decrease in cardiac output. Therefore, in an example, during the ANH-promoting mode of operation of CRM device 100, ANH pacing can be delivered intermittently, such as by using ANH pacing for a time period of about N minutes, and repeating every M minutes while in the ANH-promoting operating mode where, for example, N can be 3 and M can be 60. In another example, N can be less than one. In an example, intermittent ANH pacing can be accomplished by delivering X ANH pacing cycles for every Y total cycles where, for example, X can be 5 and Y can be 100. In an example, the Y cycles can be contiguous; in another example, the Y cycles can be non-contiguous.

In an example, intermittent ANH pacing can be accomplished by using both time periods and pacing cycles. For example, ANH pacing can be enabled 3 minutes out of every 60 minutes, and during the 3 minutes that ANH pacing is enabled, ANH pacing can be delivered 5 out of every 100 cycles. In yet another example, intermittent ANH pacing can be accomplished by delivering a specified number of ANH pacing pulses during a 24-hour period.

As described above, the dose of ANH pacing therapy can be altered by adjusting the intermittency of ANH pacing. The dose of ANH pacing therapy can also be altered by adjusting the amount of overlap between atrial and ventricular systoles. In an example, adjusting the overlap can be accomplished by changing the timing of the ventricular pacing. In another example, adjusting the overlap can be accomplished by changing one or more ventricular pacing sites. In yet another example, the dose of ANH therapy can be altered by adjusting two or more of the intermittency of ANH pacing, the timing of the ventricular pacing, and the location of ventricular pacing sites.

In FIG. 3B, time periods 302 and 306 represent normal cardiac cycles, as described above with respect to FIG. 3A. The time period 310B represents an ANH pacing cycle during which a ventricular pacing pulse is delivered at the very end of atrial diastole, such that the paced ventricular contraction is substantially concurrent with a sensed or paced atrial contraction. Thus, as shown at 312B, the AV delay can be approximately zero. Concurrent contraction of the atria and ventricles can result in blood-filled atria contracting against closed AV valves, which can cause atrial stretch and, consequently, increased secretion of ANH, such as described above.

In FIG. 3C, time periods 302 and 306 represent normal cardiac cycles, such as described above with respect to FIG. 3A. The time period 310C represents an ANH pacing cycle during which a ventricular pacing pulse is delivered during atrial diastole and in anticipation of a sensed intrinsic atrial event. In this case, because a ventricular pace is delivered before a sensed atrial beat, there is a negative AV delay, such as shown at 312C. As previously described, this can result in blood-filled atria contracting against closed AV valves, which can cause atrial stretch and, consequently, can cause increased secretion of ANH.

Although the examples in FIGS. 3A-C shows two normal cardiac cycles occurring before an ANH pacing cycle, there can be any number of normal cycles before an ANH pacing cycle occurs. Likewise, there can be one or more consecutive or non-consecutive ANH pacing cycles. In an example, there can be one or more transition cycles between a normal cardiac cycle and an ANH pacing cycle, such as described below with respect to FIG. 4.

Figure 4:
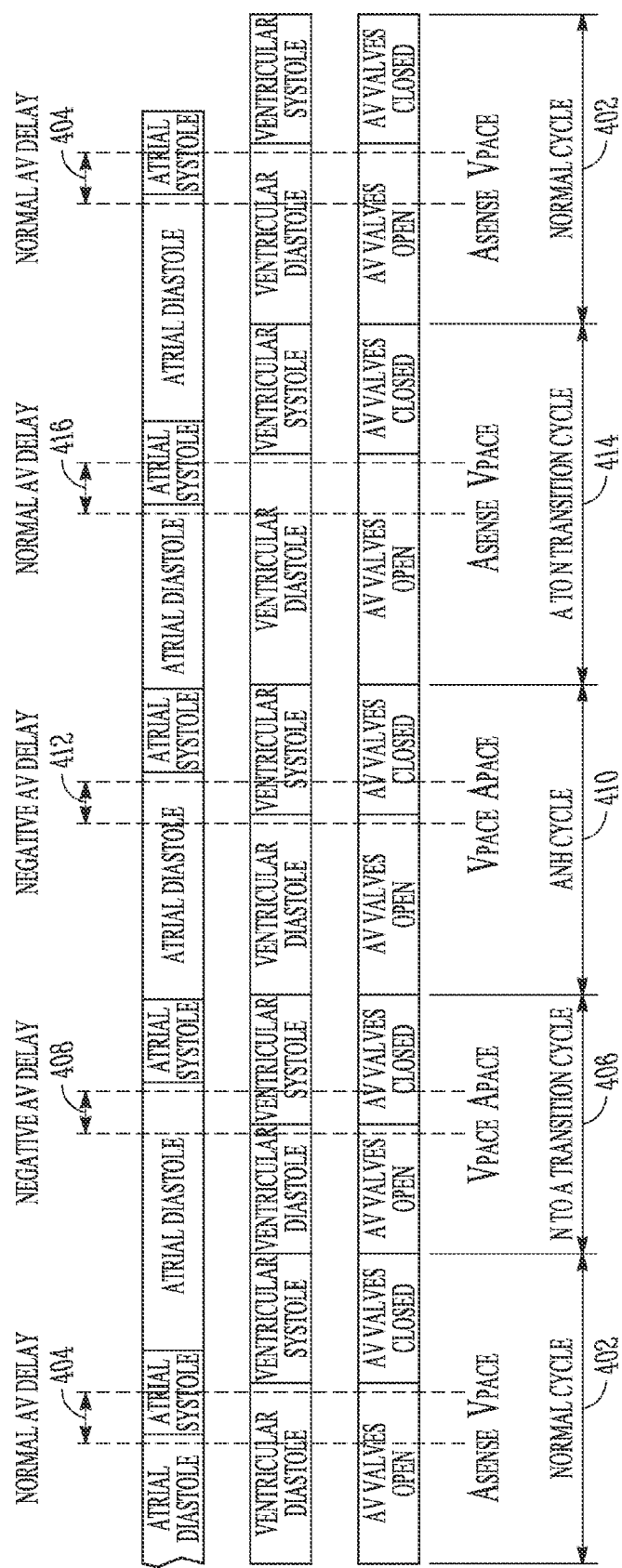
FIG. 4 is a schematic diagram illustrating generally an example of specialized ventricular pacing used to provide atrial stretch therapy.

FIG. 4 is a schematic diagram illustrating additional details of the ANH pacing example shown in FIG. 3A above. In the example shown in FIG. 4, the CRM device 100 is in the ANH-promoting operating mode. The time period 402 represents a normal cardiac cycle during normal ventricular pacing, such as described above with respect to FIGS. 3A-C. During the time period 402, the CRM device 100 can deliver ventricular pacing pulses near the end of atrial systole. In an example, during the time period 402, the CRM device 100 can sense, rather than pace, ventricular contraction events at the end of atrial systole. Similarly, although the atrial event shown during time period 402 is a sensed atrial contraction event, it can be a paced event in some examples. As shown at 404, AV delay in a normal cardiac cycle (e.g., the delay between a sensed atrial event and a paced ventricular event) can be a positive value, such as about 10-400 milliseconds, for example. In an example, there can be one or more normal cardiac cycles, such as that depicted by the time period 402, before a transition to ANH pacing occurs.

The time period 406 represents a transition cycle from a normal cardiac cycle to an ANH pacing cycle. During the time period 406, the CRM device 100 can deliver ventricular pacing pulses during atrial diastole. This results in a negative AV delay 408, such as to provide atrial stretch and augmented ANH secretion, such as described above with respect to FIG. 3A. During the time period 406, ventricular diastole can be shortened with respect to a normal cardiac cycle. This can be a result of the earlier occurrence of ventricular systole due to delivery of the ventricular pacing pulse during atrial diastole (e.g., as opposed to during atrial systole). Thus, during a transition from a normal cardiac cycle to ANH pacing, the ventricular interval can be shorter than the intrinsic atrial interval. In an example, there can be one or more transition cycles, such as that depicted by the time period 406, before ANH pacing begins. Although the atrial event shown during time period 406 is a paced event, it can be a sensed event in some examples.

Time period 410 represents an example of an ANH pacing cycle. During the time period 410, the CRM device 100 can deliver ventricular pacing pulses during atrial diastole. This results in a negative AV delay 412, such as to provide atrial stretch and augmented ANH secretion, such as described above with respect to FIG. 3A. As shown during the time period 410, ventricular diastole can lengthen with respect to ventricular diastole during the transition cycle time period 406, and can return to the length of ventricular diastole demonstrated during the normal cycle time period 402. This can be a result of ventricular "retiming," in which the ventricular cycle can be reset such that ventricular contraction events occur sooner with respect to corresponding atrial contraction events. In an example, there can be one or more ANH pacing cycles, such as that depicted by the time period 410, before transition back to a normal cardiac cycle occurs. Although the atrial event shown during time period 410 is a paced event, it can be a sensed event in some examples.

The time period 414 can represent a transition cycle from an ANH pacing cycle to a normal cardiac cycle. During the time period 414, the CRM device 100 can deliver ventricular pacing pulses at the end of atrial systole. In an example, during the time period 414, the CRM device 100 can sense, rather than pace, ventricular events at the end of atrial systole. Similarly, although the atrial contraction event shown during the time period 414 is a sensed event, it can be a paced event, in some examples. As shown at 416, AV delay in a normal cardiac cycle can be a positive value, such as a value that is between about 10-400 milliseconds, inclusive, for example. During the time period 414, ventricular diastole can be lengthened with respect to a normal cardiac cycle. This can be a result of the later occurrence of ventricular systole, compared to during ANH pacing, due to delivery of the ventricular pacing pulse during atrial systole (e.g., as opposed to during atrial diastole). Thus, during the transition from ANH pacing to a normal cardiac cycle, the ventricular interval can be longer than the intrinsic atrial interval. In an example, there can be one or more transition cycles, such as that depicted by the time period 414, before a normal cardiac cycle resumes during the time period 402.

Without being bound by theory, it is believed that it may also be beneficial to provide variability in the timing of the ANH cycle 410, such as to provide a ventricular pace concurrent with an atrial pace during a particular ANH cycle 410 and then during the next ANH cycle 410 to provide a ventricular pace just before the atrial pace and then during the next ANH cycle 410 to provide a ventricular pace just after the atrial pace, and so forth. Such variability can be deterministic, random, or pseudo-random in nature, such as can be determined by the processor circuit 212. Without being bound by theory, it is believed that just variability or randomization can help inhibit or prevent accommodation or tolerance by the physiological mechanisms responsible for generating ANH. Such variability or randomization can be implemented with respect to timing, as described above, or with respect to repetition rate, duty cycle, or any other parameter, such as for inhibiting or preventing such accommodation.

Figure 5:
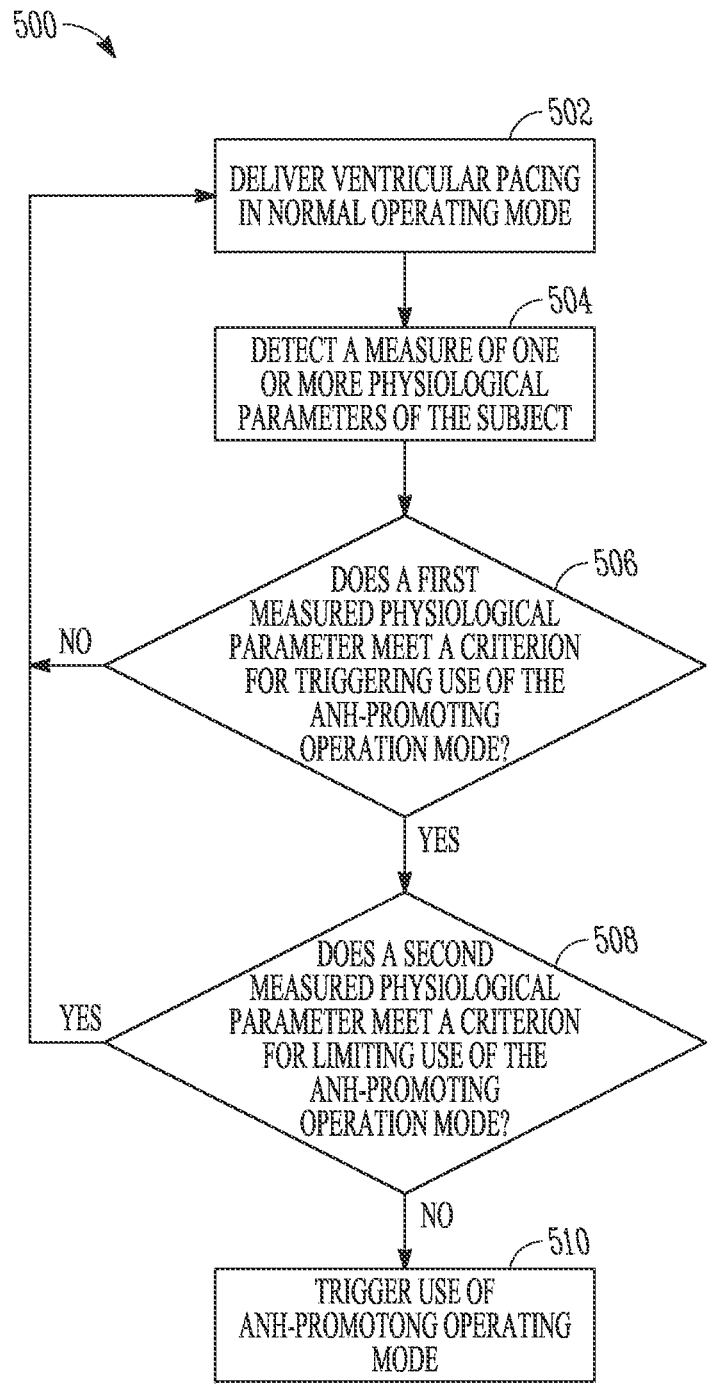
FIG. 5 is a flow chart illustrating generally a method for delivering atrial stretch therapy via intermittent specialized ventricular pacing.

FIG. 5 illustrates generally an example including a method 500 for delivering atrial stretch therapy such as via intermittent ANH pacing. In an example, the method 500 can be performed all or in part by using the CRM device 100 shown in FIG. 1. At 502, the CRM device 100 can be used to deliver ventricular pacing to a subject when in the normal operating mode, such as described above with respect to FIGS. 3A-C.

At 504, a measure of one or more physiological parameters of the subject can be detected. Examples of a physiological parameter that can be detected can include a measure of the subject's fluid status, such as a pulmonary edema level, a peripheral edema level, or a blood pressure. Other examples of a physiological parameter that can be detected at 504 can include one or more measures of the subject's hemodynamic status, such as heart rate, arrhythmia, cardiac output, canon wave, cardiac contractility, pulmonary artery pressure, heart rate variability, or sympathetic nerve activity (e.g., renal nerve sympathetic activity). Further examples of one or more physiologic parameters that can be measured can include one or more blood gases, one or more electrolytes, creatinine, blood urea nitrogen (BUN), glucose, one or more natriuretic peptides, one or more heart sounds, or one or more respirations, or any combination thereof. Another example of a physiologic parameter can include a measure a ventricular filling, such as by a thoracic impedance sensor. Another example of a physiologic parameter can include a measure of retrograde (e.g., ventricular to atrial) electrical conduction within the heart. In an example, the measure of a physiologic parameter can include a measure of the subject's physical activity level or posture, for example, using an accelerometer. In yet another example, the status of a concomitant therapy, or the patient's response to the concomitant therapy, can be measured in place of or in addition to the physiologic parameter. Examples of concomitant therapies include drug therapy, neural stimulation therapy, and cardiac resynchronization therapy.

At 506, it can be determined whether a first measured physiological parameter meets a criterion for triggering use of the ANH-promoting operating mode, such as described above with respect to FIGS. 3A-C. An example of a criterion for triggering use of the ANH-promoting operating mode can include a fluid overload condition (e.g., "hypervolemia"). A fluid overload condition can be determined, for example, by a level of pulmonary edema or peripheral edema that that exceeds a specified threshold value, such as by using an impedance-based or other fluid monitoring technique. In an example, a fluid overload condition can be determined by a blood pressure (such as can be wirelessly communicated from a separate pulmonary artery pressure (PAP) sensor) that exceeds a specified threshold value.

In an example, a criterion for triggering use of the ANH-promoting operating mode can include a fluid-underload condition (e.g., "hypovolemia"), which can be detected similarly to the fluid overload condition, such as by using a thoracic impedance monitor, a PAP monitor, or other fluid monitoring technique. In an example, the ANH-promoting operating mode can be used with the subject is euvolemic (e.g., neither fluid-overloaded nor fluid-underloaded) because, without being bound by theory, it is believed that there can be other benefits to using the ANH-promoting operating mode. For example, ANH, when attached to NPR-A receptors can obtain a variety of responses, such as vasodilation, enhanced lusitropy, anti-fibrosis, etc. Thus, the criterion for triggering use of the ANH-promoting operating mode can include detecting a condition that could benefit from such a response to the ANH-promoting operating mode. For example, detecting vasoconstriction of or beyond a specified amount can trigger the ANH-promoting mode to trigger responsive vasodilation. In an example, detecting or expecting increased cardiac contractility (such as when cardiac contractility modulation (CCM) therapy is turned on) can trigger the ANH-promoting mode to trigger responsive lusitropy to promote adequate cardiac relaxation. In an example, detecting or expecting increased myocardial fibrosis (e.g., such as can be detected by monitoring an intracardiac or thoracic impedance or otherwise) can trigger the ANH-promoting mode to trigger a responsive anti-fibrotic property of ANH.

Examples of other criteria for triggering use of the ANH-promoting operating mode can include one or more physiological parameter measurements indicative of renal dysfunction due to heart failure, such as elevated (e.g., above a normal physiologic range) creatinine or BUN, for example. In addition, use of the ANH-promoting operating mode can be triggered by a measure of one or more natriuretic peptides that is below a specified threshold value.

At 506, if it is determined that a first measured physiological parameter meets a criterion for triggering use of the ANH-promoting operating mode, then, at 508, it can be determined whether a second measured physiological parameter meets a criterion for limiting (e.g., inhibiting or avoiding) use of the ANH-promoting operating mode. In an example, the first measured physiological parameter can be different than the second measured physiological parameter. In an example, the first and second physiological parameters can be the same physiological parameter. An example of a criterion for limiting use of the ANH-promoting operating mode can include a measured indication of cardiac output that is below a specified threshold value. Other examples of criteria for limiting use of the ANH-promoting operating mode can include an indication of hypotension (e.g., blood pressure below a specified threshold value), an elevated physical activity level, an elevated respiration level, a detected arrhythmia, bradycardic pacing, or the delivery of cardiac shock therapy within a specified period of time (e.g. within the past day or within the past week). Under these conditions, ANH pacing can be limited due to the temporary decrease in cardiac output that can result from such temporary ANH pacing.

If, at 508, it is determined that a second measured physiological parameter does not meet a criterion for limiting use of the ANH-promoting operating mode, then, at 510, use of the ANH-promoting operating mode can be triggered. As described above with respect to FIGS. 3A-C, use of the ANH-promoting operating mode can include intermittent delivery of ventricular pacing pulses during an atrial diastole time period. Information about use of the ANH-promoting operating mode can be stored in a memory of the CRM device or communicated to a user or automated process, such as to provide a diagnostic indication or for use in adjusting or otherwise controlling a therapy provided by the CRM device 100, or by another implanted, ambulatory, or other medical device, or by a physician or other caregiver. Such communication can be internal to the electronics unit 102 of the CRM device 100, or can involve communication with the local interface 121 or with the remote interface 124. The acts described in FIG. 5 can be performed by the processor 212 or other circuitry in the electronics unit 102 of the CRM device 100, or by a processor or other circuitry associated with the local interface 121 or the remote interface 124, or using some combination of the CRM device 100, the local interface 121, or the remote interface 124.

At 510, use of the ANH-promoting mode can obtain the benefits described herein that are associated with increased ANH release. The present inventors have also recognized however, that delivering a ventricular pace during atrial diastole to promote ANH can lead to sub-optimal hemodynamics (e.g., reduced cardiac output) during the ANH-promoting mode. For example, if there is a risk that a subject with compromised cardiac function may become hypotensive if atrial systolic function is impacted by using the ANH promoting mode, one or more techniques to enhance cardiac output can optionally be incorporated into or used in conjunction with the ANH-promoting mode at 510.

For example, a cardiac-output compensated ANH-promoting mode at 510 can include triggering providing pacing at an increased heart rate before, during, or after the ANH-promoting mode at 510. This can help increase the cardiac output during or temporally near the ANH-promoting mode at 510, such as to compensate for what may otherwise be decreased cardiac output during the ANH-promoting mode. This can help inhibit or prevent a subject with compromised cardiac function from becoming hypotensive during the ANH-promoting mode at 510.

In an example, a cardiac-output compensated ANH-promoting mode at 510 can include triggering cardiac contractility modulation (CCM) therapy before, during, or after the ANH-promoting mode at 510. Examples of CCM are described in Stahmann U.S. patent application Ser. No. 12/561,124, entitled CARDIAC FUNCTION MANAGEMENT INTEGRATING CARDIAC CONTRACTILITY MODULATION, which was filed on Sep. 16, 2009, and which is incorporated by reference herein in its entirety, including its description of techniques (e.g., systems, methods, apparatus) of using CCM. Use of CCM can help increase the cardiac output during or temporally near the ANH-promoting mode at 510, such as to compensate for what may otherwise be decreased cardiac output during the ANH-promoting mode. This can help inhibit or prevent a subject with compromised cardiac function from becoming hypotensive during the ANH-promoting mode at 510.

In an example, a cardiac-output compensated ANH promoting mode at 510 can include initiating or changing a pharmacologic prescription (e.g., dobutamine or adenosine) before using the ANH promoting mode at 510, such as to help temporarily increase cardiac output during the ANH-promoting mode at 510, such as to inhibit or prevent the subject from becoming hypotensive.

These are just examples of techniques that can be used to compensate cardiac output during or temporally near the ANH promoting mode, and other techniques can also be used, and such techniques need not be limited to only those subjects with compromised cardiac function, but can be used in other patients.

At 504 and 506, the above description has emphasized detecting a physiological parameter and comparing it to a criterion, such as to determine whether one or more conditions exist for which ANH-promoting may be useful. However, such detecting and determining can additionally or alternatively be used to screen for or otherwise determine whether appropriate conditions exist for delivering the ANH. This can be useful, for example, such as to mitigate or avoid one or more effects or side-effects of producing ANH when operating in the ANH promoting mode at 510.

For example, ANH can have a diuretic effect, with an accompanying urge to urinate. Therefore, the engaging of the ANH promoting mode at 510 can be timed so as not to cause inconvenience to the patient—which might otherwise be the case if the ANH-promoting mode at 510 were scheduled to occur before sleep or during early hours of sleep. In an example, a sleep or posture detector can be used at 504 to determine or infer whether a patient is sleeping. One example of a sleep detector is described in Carlson et al., U.S. patent application Ser. No. 09/802,316, entitled "CARDIAC RHYTHM MANAGEMENT SYSTEM USING TIME-DOMAIN HEART RATE VARIABILITY INDICIA," which is assigned to Cardiac Pacemakers, Inc., and which is incorporated herein by reference in its entirety, including its description of a sleep detector. Another example of a sleep detector is described in Hatlestad et al., U.S. Patent Application Serial No. 2004/0073128, entitled "DETECTION OF CONGESTION FROM MONITORING PATIENT RESPONSE TO RECUMBENT POSITION," which is assigned to Cardiac Pacemakers, Inc., and which is incorporated herein by reference in its entirety. In an example, the sleep detector can be used to detect a specified sleep stage measure, such as non-rapid eye movement sleep, such as described in Stahmann et al. U.S. Pat. No. 7,572,225 entitled "SLEEP LOGBOOK," and Quan et al. U.S. Pat. No. 7,189,204 entitled "SLEEP DETECTION USING AN ADJUSTABLE THRESHOLD," both assigned to the assignee of the present patent application, the disclosures of which are incorporated herein by reference in their entirety. Sleep can also be inferred from information about physical activity, which can be detected, for example, using an accelerometer 804. Sleep can also be inferred from information about posture and angle of reclination, which can be detected using a posture detector 806, such as described in Wang et al. U.S. patent application Ser. No. 11/283,490 entitled "POSTURE DETECTOR CALIBRATION AND USE," which published on May 24, 2007 as Publication No. 2007/0118056, assigned to the assignee of the present patent application, the disclosure of which is incorporated herein by reference in its entirety.

Sleep status information can be used to schedule the ANH promoting mode at 510 to occur when the patient is awake, such as when the patient has just woken up, or just before the patient is expected to awake. Time-of-day information can constitute physiological information in the sense that it can indicate where a subject is in terms of a physiologic daily circadian rhythm. Such time-of-day information can additionally or alternatively be used, such as to time the scheduling of the ANH promoting mode at 510 to occur at an appropriate time of day, such as to appropriately coincide with the subject's circadian rhythm. Similarly, one or more other physiological conditions can be sensed at 504 and compared at 506, such as to determine whether a condition exists that indicates or contraindicates use of the ANH promoting mode at 510, so that such ANH promoting mode at 510 can be inhibited or triggered, as deemed appropriate based upon such information.

The techniques (e.g., systems, methods, apparatus) described herein can be used in conjunction with one or more other techniques for treating congestive heart failure, such as in a combination CRM device 100. Such other techniques can include, for example, one or any combination of: cardiac resynchronization therapy (CRT), such as for providing biventricular or intraventricular or other spatial coordination of a heart contraction, His bundle pacing for providing right ventricular CRT without requiring a coronary sinus or other left ventricular lead, diuretic or other drug therapy, or neurostimulation therapy such as vagal stimulation. An example of techniques for providing vagal or other neurostimulation, such as for treating congestive heart failure, is described in Moffitt et al. U.S. Pat. No. 7,499,748 entitled TRANSVASCULAR NEURAL STIMULATION DEVICE, the application for which was filed on Apr. 11, 2005, and which issued on Mar. 3, 2009, which is incorporated by reference herein in its entirety, including its description of techniques for providing neurostimulation, which can be used in a combination device with the present subject matter. Another example of techniques for providing vagal or other neurostimulation, such as for treating congestive heart failure, is described in Libbus et al. U.S. patent application Ser. No. 11/382,128, which was filed on May 8, 2006, and which published on Nov. 8, 2007 as Publication No. 2007/0260285, each of which is incorporated by reference herein in its entirety, including its description of techniques for providing neurostimulation, which can be used in a combination device with the present subject matter.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
   a cardiac rhythm management device comprising:
      a ventricular pacing circuit, configured to deliver a ventricular pace; and
      a processor circuit, coupled to the ventricular pacing circuit, the processor configured to comprise a first operating mode, the processor configured to time delivery of the ventricular pace, when in the first operating mode, so that:
      delivery of the ventricular pace is synchronized to occur during an atrial diastole time period;
      delivery of the ventricular pace results in a substantial overlap of ventricular systole and atrial systole; and
      a paced ventricular contraction is substantially concurrent with a paced or sensed atrial contraction during the same cardiac cycle.

2. The apparatus of claim 1, wherein the processor is configured to time delivery of the ventricular pace, when in the first operating mode, to cause atrioventricular valve closure during at least one of: early atrial systole or a specified period of time before atrial systole.

3. The apparatus of claim 1, comprising:
an atrial pacing circuit configured to deliver an atrial pace, and wherein the atrial. pacing circuit is coupled to the processor; and
wherein the processor is configured to time delivery of the ventricular pace, when in the first operating mode, so that a paced ventricular contraction occurs before a paced atrial contraction during the same cardiac cycle.

4. The apparatus of claim 1, comprising:
an atrial sensing circuit, coupled to the processor, and configured to sense an atrial heart signal, and wherein the atrial sensing circuit is coupled to the processor; and
wherein the processor is configured to time delivery of the ventricular pace, when in the first mode of operation, so that a paced ventricular contraction occurs before a sensed atrial contraction during the same cardiac cycle.

5. The apparatus of claim 1, comprising:
a physiologic sensor, coupled to the processor, the physiologic sensor configured to measure a physiologic parameter of a subject;
wherein the processor is configured to adjust use of the first operating mode using information about the measure of the physiologic parameter.

6. The apparatus of claim 1, comprising:
a physical activity sensor, coupled to the processor, the physical activity sensor configured to detect physical activity of a subject;
wherein the processor is configured to limit use of the first mode of operation to when the physical activity is above a specified threshold value.

7. The apparatus of claim 1, comprising:
a cardiac output monitor circuit, coupled to the processor, the cardiac output monitor circuit configured to provide an indication of a cardiac output of the subject; and
wherein the processor is configured to limit use of the first mode of operation to when the indication of the cardiac output is below a specified threshold value.

8. The apparatus of claim 1, comprising:
a fluid status monitor circuit, coupled to the processor, the fluid status monitor circuit configured to monitor a fluid status providing an indication of a fluid status of the subject; and
wherein the processor is configured to use information about the fluid status of the subject to trigger use of the first operating mode.

9. The apparatus of claim 8, wherein the processor is configured to adjust use of the first operating mode when the fluid status indicates at least one of a fluid overload condition, or a fluid underload condition.

10. The apparatus of claim 8, wherein the fluid status monitor circuit is configured to monitor the fluid status using a pulmonary artery pressure (PAP) signal received from a PAP sensor.

11. The apparatus of claim 1, wherein the processor circuit is configured to alter a delivery time of the ventricular pace, when in the first operating mode, to provide variability, with respect to an atrial contraction time, over a plurality of the ventricular paces.

12. The apparatus of claim 1, wherein the processor is configured to alter a ventricular pacing site.

13. The apparatus of claim 1, wherein the processor is configured to adjust delivery of a therapy to offset a decrease in cardiac output otherwise associated with the first operating mode.

14. The apparatus of claim 1, wherein the processor is configured to at least one of trigger or inhibit the first operating mode at least in part using information about a detected physiological condition.

15. The apparatus of claim 14, wherein the processor is configured to at least one of trigger or inhibit the first operating mode at least in part using information about a time of day, a posture, or a sleep state.

16. An apparatus comprising:
a cardiac rhythm management device comprising:
a ventricular pacing circuit, configured to deliver a ventricular pace;
a processor circuit, coupled to the ventricular pacing circuit, the processor configured to comprise a first operating mode, the processor configured to time delivery of the ventricular pace, when in the first operating mode, so that: delivery of the ventricular pace is synchronized to occur during an atrial diastole time period, and delivery of the ventricular pace results in a substantial overlap of ventricular systole and atrial systole; and
a physiologic sensor, coupled to the processor, the physiologic sensor configured to measure physiologic parameters of a subject including a physical activity, a cardiac output, and a fluid status;
wherein the processor is configured to adjust the first operating mode based on the physiologic parameters, including using information about the fluid status and limiting use of the first mode of operation to when the physical activity is above a first threshold and to when cardiac output is below a second threshold.

17. The apparatus of claim 16, wherein the processor is configured to adjust delivery of a therapy to offset a decrease in cardiac output otherwise associated with the first operating mode.

18. The apparatus of claim 16, wherein the processor is configured to at least one of trigger or inhibit the first operating mode at least in part using time of day, posture, or sleep status information.

19. A cardiac rhythm management device comprising:
a ventricular pacing circuit; and
a processor circuit coupled to the ventricular pacing circuit, the processor configured to control the ventricular pacing circuit to time delivery of a ventricular pace so that:
delivery of the ventricular pace is synchronized with an atrial diastole time period;
delivery of the ventricular pace results in overlap of ventricular systole and atrial systole; and
a paced ventricular contraction is synchronized with a paced or sensed atrial contraction during the same cardiac cycle.

20. The device of claim 19, wherein the processor configured to control the ventricular pacing circuit to time delivery of the ventricular pace so that the paced ventricular contraction is substantially concurrent with the paced or sensed atrial contraction during the same cardiac cycle.

* * * * *